United States Patent [19]

Hashimoto et al.

[11] Patent Number: 4,946,780

[45] Date of Patent: Aug. 7, 1990

[54] METHOD FOR PRODUCING SODIUM HYALURONATE BY FERMENTATION METHOD

[75] Inventors: Masamichi Hashimoto, Tokyo; Haruhisa Saegusa, Yokohama; Susumu Chiba; Hironoshin Kitagawa, both of Machida; Teruzo Miyoshi, Yokohama, all of Japan

[73] Assignee: Denkl Kagaku Kogyo Kabushiki Kaisha, Tokyo, Japan

[21] Appl. No.: 347,337

[22] Filed: May 4, 1989

[30] Foreign Application Priority Data

Oct. 12, 1988 [JP] Japan .............................. 63-254985
Mar. 9, 1989 [JP] Japan .................................. 1-54880

[51] Int. Cl.$^5$ .......................... C12P 19/04; C12R 1/46
[52] U.S. Cl. ..................................... 435/101; 435/885
[58] Field of Search ............................. 435/101, 885

[56] References Cited

U.S. PATENT DOCUMENTS

| | | | |
|---|---|---|---|
| 4,517,295 | 5/1985 | Bracke et al. | 435/885 |
| 4,582,798 | 4/1986 | Brown et al. | 435/885 |
| 4,780,414 | 10/1988 | Nimrod et al. | 435/885 |
| 4,784,990 | 11/1988 | Nimrod et al. | 435/885 |
| 4,801,539 | 1/1989 | Akasaka et al. | 435/885 |

Primary Examiner—Ronald W. Griffin
Assistant Examiner—Pamela S. Webber
Attorney, Agent, or Firm—Keil & Weinkauf

[57] ABSTRACT

A method for producing sodium hyaluronate by a fermentation method comprises culturing a mutant strain FM 100 derived from Streptococcus equi and partially free from auxotrophy to thereby stably produce sodium hyaluronate and accumulating the hyaluronate. A method for producing sodium hyaluronate by a fermentation method comprises culturing a mutant strain FM 300 derived from Streptococcus equi and partially free from auxotophy to thereby stably produce sodium hyaluronate and accumulating the hyaluronate.

32 Claims, No Drawings

METHOD FOR PRODUCING SODIUM HYALURONATE BY FERMENTATION METHOD

BACKGROUND OF THE INVENTION

This invention relates to a method for producing sodium hyaluronate by a fermentation method and, in more detail, to a method for producing and accumulating sodium hyaluronate by culturing a mutant strain derived from *Streptococcus equi* ATCC 9527 and partially free from auxotrophy.

Heretofore, sodium hyaluronate was extracted from rooster's comb, vitreous bodies of eyes of cattle or umbilical cord. However, the preparation of sodium hyaluronate by extraction has the drawback of highly complicated isolation and purification.

To overcome this drawback, there is proposed in Japanese Unexamined Patent Publications Nos. 56692/1983 and 63294/1986 a method consisting of culturing a microorganism having the ability of producing sodium hyaluronate and directly collecting sodium hyaluronate from the culture liquid. However, this method has the drawback that the amount of production is unstable from lot to lot and it is difficult to practice the method industrially. Furthermore, a solution containing sodium hyaluronate obtained by a fermentation method contains high molecular compounds and metals as impurities. Such impurities need to be separated and removed. To this end, various proposals have been made in the art, such as the method of adsorption by ion exchange resins, activated charcoal, diatomaceous earth or magnesium silicate, the method of treatment with quaternary ammonium salts or proteases, the method of extraction or precipitation by solvents such as ethanol, acetone, butanol or phenol, or the method of treatment with membrane filters.

These methods, however, are complicated in purification and are unsatisfactory for preparing sodium hyaluronate of high purity.

SUMMARY OF THE INVENTION

It is a principal object of the present invention to provide a method for preparing sodium hyaluronate easily and at a high yield.

It is another object of the present invention to provide a method for producing sodium hyaluronate which may be utilized for medicaments and by which sodium hyaluronate of high purity may be produced.

It is yet another object of the present invention to provide a method for producing sodium hyaluronate which is highly stable in production.

The above and other objects of the invention will become apparent from the following description.

According to the present invention, there is provided a method for producing sodium hyaluronate by a fermentation method comprising culturing a mutant strain FM 100 derived from *Streptococcus equi* and partially free from auxotrophy to thereby stably produce sodium hyaluronate and accumulating the hyaluronate.

According to the present invention, there is also provided a method for producing sodium hyaluronate by a fermentation method comprising culturing a mutant strain FM 300 derived from *Streptococcus equi* and partially free from auxotrophy to thereby stably produce sodium hyaluronate and accumulating the hyaluronate.

PREFERRED EMBODIMENTS OF THE INVENTION

In the present invention, the mutant strain FM 100, derived from *Streptococcus equi* and partially free from auxotrophy, may be produced by mutation of the known strain *Streptococcus equi* ATCC 9527 as the parent strain. This mutant strain FM 100 has been deposited in Fermentation Research Institute under International Deposit No. BP-2396. There is no limitation to a culture medium or culturing conditions employed in mutating the parent strain *Streptococcus equi* to the strain FM 100, if the strain FM 100 may be produced from the parent strain *Streptococcus equi*. For such mutation, for example, *Streptococcus equi* ATCC 9527 is cultured in a culture medium containing 1.5 wt. % of polypeptone, 0.5 wt. % of yeast extract and 2 wt. % of glucose at 33° C., and the strain in the log phase is collected at a lower temperature by centrifuging and washed thrice in an aseptic condition using physiological saline. The resulting cells are shaken at 30° C. for one hour in a 0.05M phosphate buffer at pH of 5.0 containing 50 μg/ml of N-methyl-N'-nitro-N-nitrosoguanidine and cooled with ice. The resulting cells are washed thrice at a lower temperature using physiological saline, cultured at 33° C. for three hours in a culture medium containing 1.5 wt. % of polypeptone, 0.5 wt. % of yeast extract and 2 wt. % of glucose, washed thrice at a lower temperature using physiological saline, and cultured at 33° C. for seven days in a first chemically defined medium shown in Table 1. The culture liquid obtained after multiplication is inoculated in a new one of the first chemically defined culture medium shown in Table 1. After repeating the above operation thrice, the resulting culture liquid is spread on a first chemically defined medium of the same composition containing agar and the resulting colony is isolated.

TABLE 1

| Components of First Chemically Defined Medium | Concentration (mg/l) | Components of First Chemically Defined Medium | Concentration (mg/l) |
|---|---|---|---|
| Glucose | 1000 | D,L-calcium Pantothenate | 0.5 |
| L-alanine | 200 | Riboflavin | 0.5 |
| L-arginine | 200 | Thiamine | 0.5 |
| L-asparagine | 200 | Niacin | 1.0 |
| L-aspartic Acid | 200 | Pyridoxamine | 1.0 |
| L-cysteine | 100 | Pryidoxal | 1.0 |
| L-glutamine | 350 | Folic Acid | 0.005 |
| L-glutamic Acid | 1000 | Biotin | 0.0025 |
| Glycine | 400 | P-aminobenzoic Acid | 0.1 |
| L-histidine | 400 | NAD | 0.5 |
| L-hydroxyproline | 50 | $K_2HPO_4$ | 500 |
| L-isoleucine | 200 | $KH_2PO_4$ | 14000 |
| L-leucine | 200 | $MgSO_4.7H_2O$ | 200 |
| L-lysine | 200 | $FeSO_4.7H_2O$ | 10 |
| L-methionine | 200 | $MnSO_4.4H_2O$ | 10 |
| L-phenylalanine | 200 | NaCl | 10 |
| L-proline | 200 | $NaC_2H_3O_2.3H_2O$ (Sodium Acetate) | 10000 |
| L-serine | 200 | | |
| L-threonine | 200 | $NaHCO_3$ | 500 |
| L-tryptophane | 200 | $CaCl_2.2H_2O$ | 60 |
| L-tyrosine | 200 | | |
| L-valine | 200 | | |
| Adenine | 20 | | |
| Guanine | 20 | | |
| Uracil | 20 | | |

Table 2 shows auxotrophy of the strain FM 100 derived from the parent strain *Streptococcus equi*. It is seen from this Table that the strain FM 100 differs from its parent strain *Streptococcus equi* in that it is partially free from auxotrophy among its bacteriological properties.

TABLE 2

| Nutrient | Demand | Nutrient | Demand | Nutrient | Demand |
| --- | --- | --- | --- | --- | --- |
| L-alanine | No | L-methionine | Yes | D,L-calcium Pantothenate | Yes |
| L-arginine | Yes | L-phenylalanine | Yes | Riboflavin | Yes |
| L-aspartic Acid | No | L-proline | No | Thiamine | Yes |
| L-cysteine | Yes | L-serine | No | Niacin | No |
| L-glutamine | Yes | L-threonine | Yes | Pyridoxamine | No |
| L-glutamic Acid | No | L-tyrosine | Yes | Pyridoxal | Yes |
| Glycine | No | L-tryptophane | Yes | Folic Acid | No |
| L-histidine | Yes | L-valine | Yes | Biotin | Yes |
| L-isoleucine | Yes | | | P-aminobenzoic Acid | No |
| L-leucine | Yes | Adenine | Yes | NAD | Yes |
| L-lysine | Yes | Uracil | No | | |

In the present invention, the strain FM 300, derived from *Streptococcus equi* and partially free from auxotrophy, is additionally free from auxotrophy with respect to the strain FM 100 derived from *Streptococcus equi*. The strain FM 300 has been deposited in the Fermentation Research Institute under the International Deposit No. BP-2319. There is no limitation to a culture medium or culturing conditions for producing the mutant strain FM 300 from its parent strain *Streptococcus equi* by mutation. For such mutation, for example, the mutant strain FM 100 of *Streptococcus equi* is produced using *Streptococcus equi* ATCC 9527 as mentioned hereinabove. The strain FM 100 thus derived by mutation from the *Streptococcus equi* is cultured in a culture medium containing 1.5 wt. % of polypeptone, 0.5 wt. % of yeast extract and 2 wt. % of glucose at 33° C., the strain in the log phase is collected at a lower temperature by centrifuging and washed thrice in an aseptic condition using physiological saline. The resulting cells are shaken at 30° C. for one hour in a 0.05M phosphate buffer at pH of 5.0 containing 50 μg/ml of N-methyl-N'-nitro-N-nitrosoguanidine and cooled with ice. The resulting cells are washed thrice at a lower temperature using physiological saline, cultured at 33° C. for three hours in a culture medium containing 1.5 wt. % of polypeptone, 0.5 wt. % of yeast extract and 2 wt. % of glucose, washed thrice at a lower temperature using physiological saline, and cultured at 33° C. for seven days in a second chemically defined medium shown in Table 3. The culture liquid obtained after multiplication is inoculated in a new one of the second chemically defined culture medium shown in Table 3. After repeating the above operation thrice, the resulting culture liquid is spread on a second chemically defined medium of the same composition containing agar and the resulting colony is isolated.

TABLE 3

| Components of Second Chemically Defined Medium | Concentration (mg/l) | Components of Second Chemically Defined Medium | Concentration (mg/l) |
| --- | --- | --- | --- |
| Glucose | 10000 | D,L-calcium Pantothenate | 0.5 |
| L-arginine | 200 | Riboflavin | 0.5 |
| L-cysteine | 100 | Thiamine | 0.5 |
| L-glutamine | 350 | Pyridoxal | 1.0 |
| L-histidine | 400 | Biotin | 0.0025 |
| L-isoleucine | 200 | NAD | 0.5 |
| L-leucine | 200 | $K_2HPO_4$ | 500 |
| L-lysine | 200 | $KH_2PO_4$ | 14000 |
| L-methionine | 200 | $MgSO_4.7H_2$ | 200 |
| L-tryptophane | 200 | $FeSO_4.7H_2O$ | 10 |
| L-tyrosine | 200 | $MnSO_4.4H_2O$ | 10 |
| L-valine | 200 | $CaCl_2.2H_2O$ | 60 |
| Adenine | 20 | | |

Table 4 shows auxotrophy of the strain FM 300 derived from the parent strain *Streptococcus equi*. It is seen from this Table that the strain FM 300 differs from its parent strain *Streptococcus equi* ATCC 9527 in that it is partially free from auxotrophy among its bacteriological properties, while also differing from the strain FM 100 derived by mutation from *Streptococcus equi* in that it is additionally free from auxotrophy in connection with the demand for L-phenylalanine and L-threonine.

TABLE 4

| Nutrient | Demand | Nutrient | Demand | Nutrient | Demand |
| --- | --- | --- | --- | --- | --- |
| L-alanine | No | L-methionine | Yes | D,L-calcium Pantothenate | Yes |
| L-arginine | Yes | L-phenylalanine | No | Riboflavin | Yes |
| L-aspartic Acid | No | L-proline | No | Thiamine | Yes |
| L-cysteine | Yes | L-serine | No | Niacin | No |
| L-glutamine | Yes | L-threonine | No | Pyridozamine | No |
| L-glumtamic Acid | No | L-tyrosine | Yes | Pyridoxal | Yes |
| Glycine | No | L-trytophane | Yes | Folic Acid | No |
| L-histidine | Yes | L-valine | Yes | Biotin | Yes |
| L-isoleucine | Yes | | | P-aminobenzoic Acid | No |
| Lleucine | Yes | Adenine | Yes | NAD | Yes |
| L-lysine | Yes | Uracil | No | | |

According to the present invention, the above described method for deriving the mutant strains FM 100 or FM 300 by mutation from their parent strain *Streptococcus equi* is merely illustrative and it suffices that the strains free from auxotrophy in the above described manner may be derived. The culture media employed for producing sodium hyaluronate using the strains thus rendered free of auxotrophy may be those customarily employed for producing microorganisms. For example, carbon sources such as glucose, fructose, galactose or sucrose, inorganic salts such as dipotassium hydrogenphosphate, potassium dihydrogenphosphate, magnesium sulfate, sodium sulfite or sodium thiosulfate, diammonium hydrogenphosphate, or organic nutrient sources, such as polypeptone, casamino acid, yeast extract, corn steep liquor or soybean hydrolysate liquid, may be employed. If necessary, various amino acids or vitamins may also be advantageously employed. These ingredients or components of the culture media may be charged collectively or divisionally, as desired.

The culturing for producing sodium hyaluronate according to the present invention may be performed by any known methods, such as culturing under aeration and agitation, and preferably at a culturing temperature of 30° to 35° C.

Since the pH of the culture liquid is lowered with the growth of the bacteria, pH adjustment agents, such as sodium hydroxide, potassium hydroxide or ammonia are preferably added to the liquid for adjusting the pH within the range from 6.5 to 9.0.

During such culturing, the culture liquid gradually increases in viscosity with production of sodium hyaluronate. Therefore, the culturing is terminated at the time point when the carbon source employed as the culture medium is used up in the culture liquid. The culture broth thus obtained is then purified to give sodium hyaluronate. When the strain FM 300, mutated from *Streptococcus equi*, is employed, a portion of the culture liquid is left after termination of culturing and a new culture medium is added thereto by way of performing semi-continuous culturing.

According to the present invention, for purifying a crude product to produce pure sodium hyaluronate after termination of culturing as mentioned hereinabove, preferably the cells are removed by centrifugation, filtration or with the aid of flocculants, carbon or celite, and then water and an organic solvent are added to the liquid to produce a cell free solution containing sodium hyaluronate, which is then subjected to a purifying process. If the solution containing sodium hyaluronate is prepared only with water without employing an organic solvent, problems are presented during the purifying process that pyrogens, proteins or metals cannot be removed sufficiently. Although any organic solvents miscible with water may be employed, such as alcohols, e.g. methanol, ethanol or propanol, or acetone, those of the grade of the reagents are preferably employed, in order that sodium hyaluronate may be used as the medicament. According to the present invention, purification may be performed by adding the aforementioned organic solvents to the solution containing sodium hyaluronate, or by dissolving sodium hyaluronate in an aqueous organic solvent of a predetermined concentration. The concentration of the organic solvent may be selected within a wide range as long as sodium hyaluronate is not precipitated. However, for most stable effects, the organic solvent is preferably contained in an amount of 20 to 50 wt. % in the solution containing sodium hyaluronate. It is also preferred that the solution containing sodium hyaluronate be diluted with water and an organic solvent so that the concentration of sodium hyaluronate in the solution is within the range from 0.1 to 5 g/l.

According to the present invention, the purification may be performed by contacting the solution containing sodium hyaluronate with alumina, activated charcoal, or "FLORISIL" manufactured by Floridin Co., Ltd. and then contacting the solution with silica gel. The alumina is preferably aluminum oxide and produced in general by dehydrating and calcining aluminum hydroxide at elevated temperatures. However, this is not limitative of the present invention.

Depending on the particle size, the alumina is classified into a fine size alumina (with the particle size of not more than 10 $\mu$m), a medium size alumina (with the particle size of 40 to 60 $\mu$m) and coarse size alumina (with the particle size of not less than 70 $\mu$m). Depending on the contents of alumina or impurities, there are various grades of alumina available on the market, such as so-called high purity alumina having the purity of about 99.99%, besides the ordinary grade alumina with the purity of 90 to 99%. There is also a so-called low soda alumina purified to have sodium oxide contents in the alumina of not higher than 0.1%, in contrast to the ordinary sodium oxide contents in alumina of 0.3 to 0.4%. There is also an activated alumina having a surface area of 50 to 400 m$^2$/g and correspondingly high adsorption properties. Any of these types of alumina may be employed in the present invention. Also, any types of alumina may be employed in the present invention without regard to the mineral types such as $\alpha$, $\beta$ or $\gamma$ or the particulate shape, such as honeycomb, granular or spherical shape.

In treating the solution containing sodium hyaluronate with alumina, the pH value of the solution containing sodium hyaluronate is preferably 3 to 10 and more preferably 6 to 9, the temperature is preferably 0° to 40° C. and the concentration of sodium hyaluronate is preferably 0.1 to 5 g/l and more preferably 0.5 to 2 g/l.

For treating the solution with alumina, the method of adding pulverulent or particulate alumina to the solution containing sodium hyaluronate and stirring the mixture in a batch-wise system, or the method of charging particulate or molded alumina into a packing column and passing the solution through the packed column, may be employed. Although these methods may be combined or performed repeatedly, it usually suffices to perform the treatment only once, depending on the selection of the treating conditions.

For contacting the solution containing sodium hyaluronate with the alumina, the packed column system is more effective than the batch type system. For treating the solution containing sodium hyaluronate by a column packed with alumina, the packed height of the column or the linear velocity of the solution may be suitably selected by taking the particle size of the alumina into account. Thus, the processing speed by the packed column system is preferably SV=0.1 to 2, in consideration of the column clogging and the processing efficiency. Although pyrogens, proteins or nucleic acids may be removed by the treatment with alumina, metallic impurities, such as magnesium, calcium, silicon, iron or aluminum cannot be removed sufficiently. Therefore, according to the present invention, the solution treated with alumina need be contacted with silica gel. When the solution containing sodium hyaluronate is contacted with silica gel, the pH of the solution is preferably 3 to 12, the temperature is preferably 0° to 40° C. and the concentration of sodium hyaluronate in the solution is preferably 0.1 to 5 g/l and more preferably 0.5 to 2 g/l. The pH value of less than 3 is not desirable since sodium hyaluronate is decomposed and the viscosity is increased to lower the operability. The pH value in excess of 12 is also not preferred since sodium hyaluronate tends to be decomposed. The temperature higher than 40° C. is also not desirable since sodium hyaluronate tends to be decomposed so that the molecular weight is lowered. The concentration of sodium hyaluronate less than 0.1 g/l is also not desired since the processing efficiency tends to be decreased and the concentration of sodium hyaluronate more than 5 g/l is also not desired since the viscosity is increased to render the operation more difficult.

According to the present invention, the silica gel is produced by decomposing sodium silicate with an inorganic acid, coagulating and washing the resulting product with water for removing impurities and drying the resulting product. However, the present invention is not limited to this method. For example, the commercially available silica gel of various grades used for dehumidification or drying in general, drying of gas or air, dehydration of organic solvents or for purification in general and having different values of particle size, pore diameter, shape, surface area or pH of the slurry, may also be employed. The particle size of 30 to 200 μm of the silica gel is preferred. If the particle size is less than 30 μm, the operability in removing the silica gel is lowered, while the column tends to be stopped when charged with the silica gel for chromatography. On the other hand, if the particle size is above 200 μm, the efficiency of removal of the metallic impurities is lowered. The silica gel preferably has the lower contents and amounts of elution of the metallic impurities.

For treating the alumina-treated solution containing sodium hyaluronate, the silica gel is packed in a packing column. The packed height of the column and the linear velocity of the solution containing sodium hyaluronate are preferably selected as a function of the particle size of the silica gel or the concentration of sodium hyaluronate. Thus, the processing speed SV is preferably 0.1 to 3.

The relative amount of the silica gel to the solution containing sodium hyaluronate need be selected as a function of the contents of the metallic impurities in the sodium hyaluronate containing solution. Usually, the silica gel is used in an amount of 10 to 300 parts by weight for purifying 1 part by weight of sodium hyaluronate.

In the method of the present invention, since sodium hyaluronate is produced by the fermentation method using a specific strain, sodium hyaluronate may be produced easily and at a high yield and stable output. Also the high purity sodium hyaluronate utilizable for medicaments may be produced by the purification process employing alumina and silica gel.

EXAMPLES OF THE INVENTION

The present invention will be explained hereinbelow in more detail with reference to Examples and Comparative Examples. However, these Examples are given for illustration only and are not intended for limiting the scope of the invention. In the following Examples and Comparative Examples, the percentage (%) denotes weight %.

EXAMPLE 1

To 1 lit. of a culture medium, pH 8.5, containing 2% of glucose, 0.2% of dipotassium hydrogenphosphate, 0.05% of magnesium sulfate heptahydrate, 0.1% of sodium thiosulfate, 1.0% of polypeptone and 0.5% of yeast extract was inoculated 10 ml of a pre-culture liquid of the mutant strain FM 300 of *Streptococcus equi* consisting of the same culture medium, and culturing was performed at the aeration of 1.5 volume volume minute (vvm), an agitating speed of 200 rpm and at the temperature of 33° C., as the pH was adjusted to 8.5 using sodium hydroxide. 2% of glucose was added after 15 hours and 900 ml of a culture liquid was extracted at the time point when the total amount of glucose was consumed. There was further added 900 ml of a medium, pH 8.5, containing 2% of glucose, 0.2% of dipotassium hydrogenphosphate, 0.05% of magnesium sulfate heptahydrate. 0.1% of sodium thiosulfate, 1.0% of polypeptone and 0.5% of yeast extract, and culturing was performed at the aeration of 1.5 volume volume minute (vvm), an agitating speed of 200 rpm and at the temperature of 33° C., as the pH was adjusted to 8.5 using sodium hydroxide. 2% of glucose was added after 5 hours and 900 ml of a culture liquid was extracted at the time point when the total amount of glucose was consumed.

Table 5 shows the yield of sodium hyaluronate when the above described semi-continuous operation was repeated five times so that the total of six batch-wise operations were performed.

The produced culture broth was adjusted to pH of 4 with hydrochloric acid, diluted by two times of volume with distilled water and freed of cells by centrifugation. The produced liquid was neutralized with sodium hydroxide and admixed with ethyl alcohol to precipitate sodium hyaluronate. After filtration, sodium hyaluronate was dissolved in water and admixed with cetyl pyridinium chloride and the produced precipitate was recovered by filtration and again dissolved in 2% saline. The resulting product was again repeatedly precipitated in ethyl alcohol. The produced sodium hyaluronate was dried in vacuum at room temperature to produce white colored sodium hyaluronate. Then, measurement of the nuclear magnetic resonance, infrared absorption spectrum and elementary analysis was performed to identify the product to be sodium hyaluronate. The following show the results of measurements.

| Elementary Analysis | C | H | N | Na |
|---|---|---|---|---|
| Calcd. (%) | 41.90 | 5.02 | 3.49 | 5.73 |
| Found (%) | 41.65 | 5.11 | 3.47 | 5.94 |

IR; 3400 cm$^{-1}$ (OH, NH), 2900 cm$^{-1}$ (CH), 1600 cm$^{-1}$ (C=O, COO−), 1560 cm$^{-1}$ (NH), 1400 cm$^{-1}$, 1040 cm$^{-1}$ $^1$H-NMR (D$_2$O) 2.0 ppm (3H), 2.6 to 4.1 (10H), 4.2 to 5.0 (2H)

TABLE 5

| Number of Batches | Yield of Sodium Hyaluronate in g (per 1 lit. of cultured liquid) |
|---|---|
| 1 | 7.3 |
| 2 | 6.8 |
| 3 | 6.9 |
| 4 | 6.9 |
| 5 | 6.5 |
| 6 | 6.7 |

EXAMPLE 2

15 l of a culture broth cultured by using a mutant strain FM 300 derived from *Streptococcus equi* was diluted to 50 l with pure water so that the concentration of sodium hyaluronate was 1.10 g/l. The centrifugation and the hollow fiber type ultrafiltration were then carried out to remove the cells and the components of the culture medium.

150 g of table salt was dissolved in 5000 ml of the solution containing sodium hyaluronate to adjust the pH to 7. The solution was then precipitated with 500 ml of ethanol, washed in 1000 ml of ethanol and dried in vacuum at 40° C. to produce 4.9 g of sodium hyaluronate. 1.0 g of the semi-purified sodium hyaluronate product was dissolved in 700 ml of water and admixed with 300 ml of ethanol to produce a mixed solution of 0.1% sodium hyaluronate. 500 ml of the mixed solution was passed through a glass column with the inside diameter of 5 cm and the height of 30 cm, packed with 150 g of 300 mesh size activated alumina for chromatography produced by Wako Pure Chemical Industries Ltd. and thoroughly washed with pure water, at a rate of SV=0.4 (60 ml/hr). The mixed solution thus treated with alumina was then passed through a second column of the same type as above packed with 150 g of silica gel manufactured by Wako Pure Chemical Industries Ltd. under the trade name of "WAKO GEL Q-50", at a rate of SV=0.7 (105 ml/hr). 500 ml of the liquid passed through the second column was collected, admixed with 15 g of table salt, adjusted to pH of 7, precipitated with 750 ml of ethanol, washed with 100 ml of ethanol and dried in vacuum at 40° C. to produce 0.48 g of sodium hyaluronate. The following analyses were conducted on the thus produced sodium hyaluronate. Table 6 shows the results of these analyses.

(1) Protein Contents: The protein contents were measured by the Lowry's method, with the purified sodium hyaluronate dissolved in 0.1N sodium hydroxide.

(2) Pyrogen Contents: The exothermic materials were measured by colorimetric analyses using a Toxicolor System produced by Seikagaku Kogyo Co., Ltd.

(3) Metals: The metals were measured by a photographic dry plate system using an emission spectroanalytic system manufactured by Nippon Jarrell-Ash Co., Ltd.

COMPARATIVE EXAMPLE 1

Sodium hyaluronate was purified and analyzed by the same method as that shown in Example 2, except using water in place of ethanol, with the exception of ethanol used for precipitation. The results are shown in Table 6.

TABLE 6

| Analyzed Item | Ex. 2 | Comp. Ex. 1 |
|---|---|---|
| Protein Contents | 0.003% | 0.08% |
| Pyrogen Contents | 5 pg/mg | 97 pg/mg |
| Metals | | |
| Aluminum | Not More Than 10 ppm | 100 t0 1000 ppm |
| Silicon | Not More Than 10 ppm | 100 ppm |
| Iron | Not More Than 10 ppm | 10 to 100 ppm |
| Magnesium | Nearly Zero | 10 ppm |

EXAMPLE 3

To 1 lit. of a culture medium, pH 8.5, containing 2% of glucose, 0.2% of dipotassium hydrogenphosphate, 0.05% of magnesium sulfate heptahydrate, 0.1% of sodium thiosulfate, 1.0% of polypeptone and 0.5% of yeast extract was inoculated 10 ml of a pre-culture liquid of the mutant strain FM 100 derived from *Streptococcus equi* consisting of the same culture medium as above, and culturing was performed at the aeration of 1.5 volume volume minute (vvm), an agitating speed of 200 rpm and at the temperature of 33° C., as the pH was adjusted to 8.5 using sodium hydroxide. 2% of glucose was added after 15 hours and the culturing was terminated at the time point when the total amount of glucose was consumed.

The culture broth was adjusted to pH of 4 with hydrochloric acid, diluted by two times of volume with distilled water and freed of the cells by centrifugation. The produced cell free liquid was admixed with ethyl alcohol to precipitate sodium hyaluronate. After filtration, sodium hyaluronate was dissolved in water and admixed with cetyl pyridinium chloride and the produced precipitate was recovered by filtration and again dissolved in 2% saline. The resulting product was repeatedly precipitated in ethyl alcohol. The produced sodium hyaluronate was dried in vacuum at room temperature to produce 7.2 g of white colored sodium hyaluronate per lit. of the culture liquid. Then, measurement of nuclear magnetic resonance, infrared absorption spectrum and elementary analysis was performed to identify the product to be sodium hyaluronate. The following show the results of the measurements.

| Elementary Analysis | C | H | N | Na |
|---|---|---|---|---|
| Calcd. (%) | 41.90 | 5.02 | 3.49 | 5.73 |
| Found (%) | 41.78 | 5.00 | 3.48 | 5.83 |

IR; 3400 cm$^{-1}$ (OH, NH), 2900 cm$^{-1}$ (CH), 1600 (C=O, COO$^-$), 1560 cm$^{-1}$ (NH), 1400 cm$^{-1}$, 1040 cm$^{-1}$ $^1$H-NMR (D$_2$O) 2.0 ppm (3H), 2.6 to 4.1 (10H), 4.2 to 5.0 (2H)

The culturing operations similar to that described above was performed four additional times so that five batch-wise operations were performed. The results are shown in Table 7.

TABLE 7

| Number of Batches | Yield of Sodium Hyaluronate in g (per 1 lit. of culture liquid) |
|---|---|
| 1 | 7.2 |
| 2 | 7.1 |
| 3 | 7.0 |
| 4 | 7.3 |
| 5 | 7.1 |

After prolonged culturing, the yield of sodium hyaluronate remained perpetually stable.

COMPARATIVE EXAMPLE 2

Five times of operations, each similar to that of Example 1, were conducted, using the parent strain *Streptococcus equi* ATCC 9527, in place of the mutant strain FM 100 of the *Streptococcus equi*. Sodium hyaluronate was produced in amounts of 4.5 g, 2.3 g, 3.5 g, 1.2 g and 3.9 g, which were low and showed marked dispersions as compared with Example 3.

EXAMPLE 4

15 l of a culture broth cultured by using the mutant strain FM 100 of *Streptococcus equi* was diluted to 50 l with pure water so that the concentration of sodium hyaluronate was 1.10 g/l. The centrifugation and the hollow fiber type ultrafiltration were then carried out to remove the cells and the components of the culture medium.

150 g of table salt was dissolved in 5000 ml of the solution containing sodium hyaluronate to adjust the pH to 7. The solution was then precipitated with 500 ml of ethanol, washed in 1000 ml of ethanol and dried in vacuum at 40° C. to produce 4.9 g of sodium hyaluronate. 1.0 g of the semi-purified sodium hyaluronate product was dissolved in 700 ml of water and admixed with 300 ml of ethanol to produce a mixed solution of 0.1% sodium hyaluronate and ethanol. 500 ml of the mixed solution was passed through a column with the inside diameter of 11.3 cm and the height of 15 cm, packed with 300 g of alumina produced by Showa Denko KK under the trade name of "A-13-S" and thoroughly washed with 30% ethanol, at a rate of SV=0.2 (60 ml/hr). The mixed solution thus treated with alumina was then passed through a second column of the same type as above packed with 150 g of silica gel manufactured by Wako Pure Chemical Industries Ltd. under the trade name of "WAKO GEL Q-50", at a rate of SV=0.7 (105 ml/hr). 500 ml of the liquid passed through the second column was collected, admixed with 15 g of table salt, adjusted to pH of 7, precipitated with 750 ml of ethanol, washed with 100 ml of ethanol and dried in vacuum at 40° C. to produce 0.4 g of sodium hyaluronate. The contents of proteins and the pyrogens in the produced sodium hyaluronate were measured in the same way as in Example 2, and the nucleic acid analysis was performed by measuring the absorptivity at 260 nm of the 0.1% sodium hyaluronate solution. The results are shown in Table 8.

COMPARATIVE EXAMPLE 3

Sodium hyaluronate was purified and analyzed by the same method as that shown in Example 4, except using water in place of ethanol, with the exception of ethanol used for precipitation. Te results are shown in Table 8.

EXAMPLE 5

Sodium hyaluronate was purified and analyzed by the same method as that shown in Example 3, except using acetone in place of ethanol, with the exception of ethanol used for precipitation. The results are shown in Table 8.

TABLE 8

| Analyzed Item | Ex. 4 | Ex. 5 | Comp. Ex. 3 |
| --- | --- | --- | --- |
| Protein Contents | 0.01% | 0.01% | 0.10% |
| Pyrogen Contents | Not More Than 10 pg/mg | Not More Than 10 pg/mg | 100 pg/mg |
| Nucleic Acid | Not Detected | Not Detected | Not Detected |

In Comparative Example 3, sodium hyaluronate of the comparable quality as that in Example 4 could occasionally be produced but only with poor reproducibility. Table 8 shows the average values of the measured results.

EXAMPLE 6

Sodium hyaluronate was purified in the same way as in Example 2 except using the mutant strain FM 100 of Streptococcus equi in place of the mutant strain FM 300 of Streptococcus equi to produce 0.40 g of sodium hyaluronate, which was then analyzed in the same way as in Example 2. The results are shown in Table 9.

COMPARATIVE EXAMPLE 4

Sodium hyaluronate was purified and analyzed by the same method as that shown in Example 6, except using water in place of ethanol, with the exception of ethanol used for precipitation. The results are shown in Table 9.

TABLE 9

| Analyzed Item | Ex. 6 | Comp. Ex. 4 |
| --- | --- | --- |
| Protein Content | 0.004% | 0.09% |
| Pyrogen Contents | Not More Than 10 pg/mg | 89 pg/mg |
| Metals | | |
| Aluminum | Not More Than 10 ppm | 10 to 1000 ppm |
| Silicon | Not More Than 10 ppm | 100 ppm |
| Iron | Not More Than 10 ppm | 10 to 100 ppm |
| Magnesium | Nearly Zero | 10 ppm |

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. Streptococcus equi FERM BP-2396.
2. Streptococcus equi FERM BP-2319.
3. A microorganism having the identifying characteristics of Streptococcus equi FERM BP-2396 which is capable of producing sodium hyaluronate in a culture medium.
4. A microorganism having the identifying characteristics of Streptococcus equi FERM BP-2319 which is capable of producing sodium hyaluronate in a culture medium.
5. A process for preparing sodium hyaluronate comprising obtaining a microorganism having the identifying characteristics of Streptococcus equi FERM BP-2396 or Streptococcus equi FERM BP-2319, culturing said microorganism in a culture medium to stably produce sodium hyaluronate and recovering sodium hyaluronate from said culture medium.
6. A process for preparing sodium hyaluronate of high comprising:
   obtaining microbial cells having the identifying characteristics of Streptococcus equi FERM BP-2396 or Streptococcus equi FERM BP-2319,
   culturing the cells in a culture medium to stably produce sodium hyaluronate,
   separating the cells from culture medium to produce cell-free culture broth containing sodium hyaluronate,
   adding alcohol to the culture broth containing sodium hyaluronate to precipitate sodium hyaluronate,
   separating the precipitated sodium hyaluronate,
   adding water and alcohol to the precipitate to dissolve the sodium hyaluronate thereby producing a solution containing sodium hyaluronate,
   contacting said solution containing sodium hyaluronate with alumina, activated charcoal or mixtures thereof and then with silica to form a purified solution of sodium hyaluronate,
   adding alcohol to the purified solution of sodium hyaluronate to precipitate purified sodium hyaluronate and
   drying said purified sodium hyaluronate.
7. The process of claim 5, wherein said microorganism is Streptococcus equi FERM BP-2396.

8. The process of claim 5, wherein said microorganism is *Streptococcus equi* FERM BP-2319.

9. The process of claim 5, wherein said microorganism is cultured in a medium comprising inorganic salts, organic nutrient sources, amino acids, vitamins or mixtures thereof and at least one carbon source.

10. The process of claim 9, wherein the components of the culture medium are charged collectively or are divided and charged separately.

11. The process of claim 5, wherein said microorganism is cultured at a temperature of 30° to 35° C.

12. The process of claim 5, wherein the pH of the culture medium is adjusted to a pH of 6.5 to 9.0.

13. The process of claim 12, wherein sodium hydroxide, potassium hydroxide, ammonium or mixtures thereof is used to adjust the pH of the culture medium.

14. The process of claim 5, wherein the culturing of the microorganism is discontinued when the carbon source in said culture medium has been consumed.

15. The process of claim 5 wherein the recovered sodium hyaluronate is purified.

16. The process of claim 5, wherein the sodium hyaluronate is recovered from the culture medium by separating the cells from the culture medium to produce a cell-free culture broth containing sodium hyaluronate, adding water and an organic solvent to produce a solution containing sodium hyaluronate and purifying the solution containing sodium hyaluronate.

17. The process of claim 16, wherein the concentration of sodium hyaluronate in said solution containing sodium hyaluronate is 0.1 to 5 g/l.

18. The process of claim 16, wherein said organic solvent is selected from the group consisting of methanol, ethanol, propanol, acetone and mixtures thereof.

19. The process of claim 16, wherein the concentration of the organic solvent added is selected so as to not precipitate the sodium hyaluronate.

20. The process of claim 16, wherein the purification is performed by contacting the solution containing sodium hyaluronate with a substance selected from the group consisting of alumina, activated charcoal and mixtures thereof and subsequently with silica gel.

21. The process of claim 20, wherein the solution containing sodium hyaluronate is contacted with alumina at a pH of 3 to 10 and a temperature of 0° to 40° C.

22. The process of claim 20, wherein the silica gel is used in an amount of 10 to 300 parts by weight to 1 part by weight of sodium hyaluronate.

23. The process of claim 20, wherein the silica gel is contacted at a pH of 3 to 12 and at a temperature 0° to 40° C.

24. The process of claim 20, wherein the solution containing sodium hyaluronate is contacted with alumina by packing a column with alumina and passing said solution through the packed column.

25. The process of claim 24, wherein the solution containing sodium hyaluronate is passed through the packed column at a speed of SV=0.1 to 2.

26. The process of claim 20, wherein the solution containing sodium hyaluronate is contacted with alumina by a batch system and by packing a column with alumina.

27. The process of claim 26, wherein the solution containing sodium hyaluronate is passed through said column at a speed of SV=0.1 to 2.

28. The process of claim 20, wherein the silica gel has a particle size of 30 to 200 μm.

29. The process of claim 20, wherein the solution is contacted with silica gel by using a column.

30. The process of claim 29, wherein the solution containing sodium hyaluronate is passed through said column at a speed of SV=0.1 to 2.

31. The process of claim 5, wherein said microorganism is prepared by mutating an auxotrophic *Streptococcus equi* with N-methyl-N'-nitro-N-nitrosoguanidine, culturing the mutated cells in a culture medium consisting essentially of glucose, L-alanine, L-arginine, L-asparagine, L-aspartic acid, L-cysteine, L-glutamine, L-glutamic acid, glycine, L-histidine, L-hydroxyproline, L-isoleucine, L-leucine, L-lysine, L-methionine, L-phenylalanine, L-proline, L-serine, L-threonine, L-tryptophane, L-tyrosine, L-valine, adenine, guanine, uracil, D,L-calcium pantothenate, riboflavin, niacin, pyridoxamine, pyridoxal, folic acid, biotin, p-aminobenzoic acid, NAD, $K_2HPO_4$, $KH_2PO_4$, $MgSO_4.7H_2O$, $FeSO_4.7H_2O$, $MnSO_4.4H_2O$, NaCl, $NaC_2H_3O_2.3H_2O$, $NaHCO_3$ and $CaCl_2.2H_2O$, and isolating a microorganism partially free from auxotrophy and having the identifying characteristics of *Streptococcus equi* FERM BP-2396.

32. The process of claim 5, wherein said microorganism is prepared by mutating a microorganism partially free from auxotrophy and having the identifying characteristics of *Streptococcus equi* FERM BP-2396 with N-methyl-N'-nitro-N-nitrosoguanidine, culturing the mutated cells in a culture medium consisting essentially of glucose, L-arginine, L-cysteine, L-glutamine, L-histidine, L-isoleucine, L-leucine, L-lysine, L-methionine, L-tryptophane, L-tyrosine, L-valine, adenine, D,L-calcium pantothenate, riboflavin, thiamine, pyridoxal, biotin, NAD, $K_2HPO_4$, $KH_2PO_4$, $MgSO_4.7H_2O$, $FeSO_4.7H_2O$, $MnSO_4.4H_2O$ and $CaCl_2.2H_2O$, and isolating a microorganism partially free from auxotrophy and having the identifying characteristics of *Streptococcus equi* FERM BP-2319.

* * * * *

UNITED STATES PATENT AND TRADEMARK OFFICE
CERTIFICATE OF CORRECTION

PATENT NO. : 4,946,780

DATED : August 7, 1990

INVENTOR(S) : Masamichi HASHIMOTO et al.

It is certified that error appears in the above-identified patent and that said Letters Patent is hereby corrected as shown below:

Column 12, line 43,
Claim 6, Line 2 : after "high" insert --purity--

Column 12, line 49,
Claim 6, Line 8: after "produce" insert --a--
Column 14, line 19,
Claim 30, Line 3: "2" should read --3--

Signed and Sealed this

Twenty-sixth Day of November, 1991

Attest:

HARRY F. MANBECK, JR.

Attesting Officer

Commissioner of Patents and Trademarks